(12) United States Patent
Biber

(10) Patent No.: US 8,704,519 B2
(45) Date of Patent: Apr. 22, 2014

(54) MAGNETIC RESONANCE TOMOGRAPHY APPARATUS AND METHOD WHEREIN THE POSITION OF A LOCAL COIL IS DETECTED BY REFLECTED ELECTROMAGNETIC WAVES

(75) Inventor: Stephan Biber, Erlangen/Frauenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 684 days.

(21) Appl. No.: 12/690,422

(22) Filed: Jan. 20, 2010

(65) Prior Publication Data

US 2010/0182005 A1 Jul. 22, 2010

(30) Foreign Application Priority Data

Jan. 20, 2009 (DE) .......................... 10 2009 005 188

(51) Int. Cl.
*G01R 33/341* (2006.01)

(52) U.S. Cl.
USPC ........... 324/318; 324/309; 324/307; 600/414; 600/415; 600/426

(58) Field of Classification Search
USPC .......... 324/300–322; 600/407–432, 310, 160; 382/128–131; 343/700 MS; 356/479, 356/614
See application file for complete search history.

(56) References Cited

U.S. PATENT DOCUMENTS

| 3,531,705 | A | * | 9/1970 | Rosin et al. | 318/567 |
|---|---|---|---|---|---|
| 6,485,413 | B1 | * | 11/2002 | Boppart et al. | 600/160 |
| 7,180,294 | B2 | | 2/2007 | Kohlmüller | 324/318 |
| 7,474,407 | B2 | * | 1/2009 | Gutin | 356/479 |
| 7,598,737 | B2 | * | 10/2009 | Campagna | 324/307 |
| 7,911,209 | B2 | * | 3/2011 | Alradady et al. | 324/318 |
| 8,390,290 | B2 | * | 3/2013 | Sukkau | 324/318 |
| 8,452,374 | B2 | * | 5/2013 | Ma et al. | 600/415 |
| 2002/0118373 | A1 | * | 8/2002 | Eviatar et al. | 356/614 |
| 2005/0054910 | A1 | * | 3/2005 | Tremblay et al. | 600/411 |
| 2006/0132790 | A1 | * | 6/2006 | Gutin | 356/479 |
| 2008/0108892 | A1 | | 5/2008 | Ritter | 600/410 |
| 2010/0156421 | A1 | * | 6/2010 | Sukkau | 324/318 |
| 2010/0182005 | A1 | * | 7/2010 | Biber | 324/307 |
| 2011/0034796 | A1 | * | 2/2011 | Ma et al. | 600/407 |
| 2011/0178379 | A1 | * | 7/2011 | Dudhia et al. | 600/310 |
| 2011/0230755 | A1 | * | 9/2011 | MacFarlane et al. | 600/414 |
| 2012/0212375 | A1 | * | 8/2012 | Depree, IV | 343/700 MS |

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

A magnetic resonance tomography device has a local coil that is fashioned to receive a magnetic resonance signal. This device has a detector system that is fashioned to detect a position of the local coil on the basis of electromagnetic waves that are affected by the position of the local coil and can be differentiated from the magnetic resonance signal. A method to detect a position of a local coil in a magnetic resonance tomography device Is implemented in this manner as well.

13 Claims, 9 Drawing Sheets

MAGNETIC RESONANCE TOMOGRAPHY APPARATUS AND METHOD WHEREIN THE POSITION OF A LOCAL COIL IS DETECTED BY REFLECTED ELECTROMAGNETIC WAVES

BACKGROUND OF THE INVENTION

1. Field of the Invention

The invention concerns a magnetic resonance tomography apparatus with a local coil that is fashioned to receive a magnetic resonance signal, and with a detector system that is fashioned to detect a position of the local coil. Moreover, the invention concerns a method to detect a position of a local coil in a magnetic resonance tomography device, the local coil being fashioned to receive a magnetic resonance signal.

2. Description of the Prior Art

Magnetic resonance tomography is a technique in widespread use for the acquisition of images of the inside of the body of a living examination subject. In order to acquire an image with this method, i.e. to generate a magnetic resonance exposure of an examination subject, the body or a body part of the patient that is to be examined must initially be exposed to an optimally homogeneous, static basic magnetic field that is generated by a basic field magnet of the magnet system of the magnetic resonance tomography device. Rapidly switched gradient fields for spatial coding that are generated by gradient coils of the magnet system are and overlaid on this basic magnetic field during the acquisition of the magnetic resonance images. Moreover, RF pulses of a defined field strength are radiated into the examination volume (in which the examination subject is located) with a radio-frequency antenna. The nuclear spins of the atoms in the examination subject are excited by means of these RF pulses such that they are deflected out of their equilibrium state (which runs parallel to the basic magnetic field) by an amount known as an "excitation flip angle". The nuclear spins then process around the direction of the basic magnetic field. The magnetic resonance signals that are thereby generated are acquired by radio-frequency reception antennas. The reception antennas can either be the same antennas with which the radio-frequency pulses are also radiated or separate reception antennas. A better signal-to-noise ratio is obtained with the use of separate reception antennas. To further improve the signal-to-noise ratio of high resolution images, antenna systems known as high field systems are used that are operated at a basic magnetic field of 3 Tesla. A magnetic resonance tomography device (MRT device) suitable for the magnetic resonance data acquisition as described has a stationary magnet system that embodies the coils necessary to generate the different fields.

Typically it is necessary that more reception antennas should be connected to a receiver system to receive coil signals of the reception antennas than there are receivers provided. This is achieved with the use of a switching matrix that is connected between the receiver system and the reception antennas. The switching matrix relays to the receiver system only the receiver signals that originate from those reception antennas that should actually be active. This procedure is useful because the magnet system has a limited homogeneity volume only in a region of its isocenter, and this homogeneity volume is sometimes relatively short (for example 20 to 40 cm) in relation to the length of the stationary magnet system and the length of a person being examined (who can be covered by a number of reception antennas). The field of view in which respective image data are acquired should lie within this homogeneity volume. It is therefore the goal that signals only from those reception antennas that are located in the homogeneity volume should be read out. However, for this purpose the positions of the individual reception antennas must be determined sufficiently precisely, and in particular it must be decided whether they are positioned within the homogeneity volume or not. The separate reception antennas—also called local coils and abbreviated in the following as coils—can be divided into two classes, namely into stationary coils and non-stationary coils.

Due to their mechanical design, the stationary coils can only be attached to the patient table at specific positions and there act as a head coil or spinal column coil, for example. Cardiac coils or knee coils (for example) that, due to their design, are not necessarily bound to a specific site on the bed or the patient fall in the class of non-stationary coils. These non-stationary coils are usually located on the patient (anterior). Knee coils can be alternately used for the left or right knee. Additional examples of non-stationary coils are abdomen coils, wrist coils, shoulder coils, etc. Such non-stationary coils are typically used in order to achieve an optimally flexible adaptation to the respective anatomy of the patient and play an important role in modern magnetic resonance tomography.

With regard to the identification and localization of stationary coils, it is necessary for the MRT device to precisely identify the type of coil, which is uniquely identified by an electrical code that is transmitted after a connection of the coil to the MRT device, and to unambiguously predetermine the location of the coil, since this is integrated into the patient bed or attached to it. For example, if the patient bed is driven into the stationary magnet system, the position knowledge of the stationary coil is obtained due to the precise position knowledge of the patient bed as well as its speed. By contrast, the non-stationary coils are characterized in that, although which coil type is connected is known to the MRT device via the transmission of a code, any spatial information regarding this coil is absent for the MRT device.

Since, as noted above, reception signals of a coil can only be meaningfully evaluated if it is ensured that this coil is located in the homogeneity volume of the magnet system, an optimally precise determination and knowledge of the position of the coil is indispensable.

The position of the non-stationary coil is typically determined by magnetic resonance measurements (data acquisitions). For this purpose, the components of the MRT device that are used to conduct the magnetic resonance measurement form a detector system to detect the position of the local coil. Since the MRT device has no a priori knowledge about the position of the non-stationary coil on the bed or on the patient, this must initially be "searched for" through a series of such magnetic resonance measurements. The patient bed, with the patient located thereupon with the non-stationary coils, is thereby brought into various z-positions along the longitudinal direction of the magnet system within the magnet system and a magnetic resonance experiment is conducted at the respective z-positions. The position of the non-stationary coils can be derived from the series of the reception signals that is obtained in this way.

However, certain basic conditions must be complied with in order to implement this method for coil position detection. For example, the entire workflow must be organizes with the necessity of conducting the coil position detection being taken into account, because the implementation of the magnetic resonance measurement therefore takes time, and protective measures against interference radiation and signals from the outside must be taken. Typically a magnetic resonance system has a shielding chamber in which the MRT device, the patient bed and the local coils are located. To avoid interference radiation, the door to the shielding chamber must be closed, for example. For this purpose the technician supervising the procedure must leave the room after the patient preparation and close the door after himself, herself or close it from the inside, so that the movement of the bed or of the patient can at least be visually monitored by this person technician during the coil position detection.

Additionally, such coil position determinations with magnetic resonance experiments are problematical if the coil to be localized is located outside or at the edge of the homogeneity volume.

SUMMARY OF THE INVENTION

An object of the present invention is to further develop a magnetic resonance tomography device of the aforementioned type and a method to detect the position of a local coil of such a system, such that a detection of the coil position can ensue without involvement of the technician to observe the basic conditions cited above.

According to the invention, a magnetic resonance tomography device has a detector system that is fashioned to detect a position of a local coil wherein the detection ensues on the basis of electromagnetic waves that are affected (altered) by the position of the local coil and that can be differentiated from the magnetic resonance signal. Furthermore, in a method according to the invention to detect a position of a local coil in a magnetic resonance tomography device, wherein the local coil is fashioned to receive a magnetic resonance signal, the detection of the position of the local coil ensues on the basis of electromagnetic waves that are affected by the position of the local coil and that can be differentiated from the magnetic resonance signal.

The electromagnetic waves that can be differentiated from the magnetic resonance signal are waves that are not caused by the magnetic resonance measurement (data acquisition). They are inasmuch thus differentiable from the magnetic resonance signal because they have a different cause than the magnetic resonance data that are embodied in the magnetic resonance signal. To generate them, the radio-frequency system of the magnetic resonance tomography device is not used in a typical manner; rather, a light source or the like is used, for example.

By avoiding the magnetic resonance data acquisition, the basic conditions that are necessary in the prior art techniques for the coil position detection can essentially be completely ignored because the results are no longer depend on these conditions. It is thus irrelevant whether a local coil is positioned within the homogeneity volume. An accelerated workflow is therefore provided without unwanted interruptions to detect the local coil because the magnetic resonance measurement is foregone and possible interference signals that could affect the magnetic resonance experiment do not need to be considered. The results of the position determination of the local coil are additionally independent of the gradient field and the sensitivity profile. A significantly more robust solution for the detection of the position of the local coil is thus achieved. In summary, the advantages achieved by the measures according to the invention are in the areas of precision, speed and insensitivity to environmental parameters.

With regard to the electromagnetic waves that are used, it has proven to be particularly advantageous for the detector system to be fashioned to process electromagnetic waves that propagate optically or quasi-optically. This enables the realization of a relatively precise beam direction or a beam path with which the detection can be implemented with the required precision. Light waves are advantageously used.

As is explained below in detail, natural light or general environmental (ambient) light (for example) can also be used to detect the position. According to one exemplary embodiment of the invention, however, the detector system has a signal source device that is fashioned to emit the electromagnetic waves. In the detection of the position of the local coil it is thereby ensured that both the position of the signal source—thus also the location from which the waves are emitted—and the parameters of the waves themselves are well defined and known. For the purpose of generating the electromagnetic waves, the signal source device can have various elements such as an LED, incandescent lamp, laser source, discharge tube or a source for shortwave radio waves (preferably in a frequency range from 20 GHz to 5 THz). However, combinations of such elements can also be provided. For example, if a light source is used, this can emit visible light, infrared light or even ultraviolet light. The selection of the respective element or the combination of the elements thus does not need to be adapted to the respective design specifications, allowing other considerations—for example focusing capability of the electromagnetic waves generated with the aid of the respective element or, respectively, reflection behavior or reception capability or, respectively, processing capability etc.—to play a role.

In particular if the signal source device is mounted on the scanner, it has proven to be particularly advantageous for the signal source device to be fashioned to generate a beam of the emitted electromagnetic waves that exhibits a first aperture angle in a first direction, for example in the x-direction (direction transverse to the limit frequency of the patient bed), and a second aperture angle in a second direction, for example the z-direction (longitudinal direction of the patient bed). The beam can therefore be significantly bundled in one plane and only weakly bundled in the other plane, such that an exposure band essentially results on the exposed subject (for example the patient or test subject or the local coil positioned thereon) when the beam passes this. For example, if the patient bed with the patient lying thereupon and the local coil positioned on the patient is now moved along the z-direction, a relatively precise spatial resolution in this direction can be achieved by the narrow bundling in the z-direction. By contrast, it is relatively immaterial in which x-position the local coil is positioned because the local coil is exposed in any case due to the relatively large exposure region in the x-direction that preferably extends across the entire width of the patient bed.

According to a preferred exemplary embodiment of the invention, the detector system has a reflection device that is located on the outside of the local coil (thus on the side facing away from the patient) and is fashioned to reflect the electromagnetic wave. This reflection device enables electromagnetic waves that are emitted (for example from the signal source device that is attached to the tomography or to an outer region of its housing) to be reflected in a specific manner. For example, the reflection device can have a reflection strip or point of whatever design (or very generally a region) that exhibits a reflection response that can be differentiated from its environment.

According to a preferred exemplary embodiment of the invention, the reflection device has an encoding structure in order to encode the position of the local coil and/or an orientation of the local coil and/or a type of local coil in the reflected waves. This allows every individual local coil to be precisely identified in an optical manner or, respectively, its position and/or its bearing to be precisely detected.

Such an (optical) encoding structure can be formed, for example, by two highly reflective surfaces running transversal to the z-direction that, for their part, are embedded in a non-reflective or, respectively, less reflective surface. Depending on the use case or the result to be achieved, practically no limits are placed on the embodiment of the encoding structure. Accordingly more than two highly reflective areas or bands of equal width and equal length and running transversal to the z-direction can also be provided. Furthermore, not only continuous highly reflective areas running transversal to the z-direction but also highly reflective areas interrupted by non-reflective or, respectively, less reflective areas are possible. The shape of the highly reflective areas can additionally also deviate from a rectangular or, respectively, square shape and, for example, be executed round or triangular or possibly possess more than four corners. However, very generally any arbitrarily shaped region can be used. The reflection capability itself can also be used for encoding if, for example, highly reflective regions are combined with less strongly reflective regions. Highly reflective regions with diffusely scattering regions can also be used, or even only diffusely scattering regions. The respective selected encoding structure will ultimately be dependent on the required detection capability or on the required information content or on the information depth of this structure.

An additional aspect of the reflection device concerns a surface structure of the reflection device that, in a preferred embodiment, is with the use of a retroreflector. A retroreflector has the property that its reflection behavior is largely independent of the alignment of the reflector, and the reflection for the most part ensues back to the radiation source (thus opposite to the direction of incidence). Retroreflectors exist in different embodiments. In addition to plane-optical angle reflectors, reflex reflectors, triple mirrors and triple prisms, there are rotationally symmetrical lens reflectors (cat's eyes, Lüneberg lenses) and even in principle other types of retroreflective bodies (for example biconical designs).

The plane-optical retroreflectors consist of plane mirrors and plane surfaces. In this class differentiation is made between embodiments with two or three reflective planes standing perpendicular to one another. In particular, light from the three spatial directions can be reflected by the use of three reflective planes standing perpendicular to one another.

Such a structure (that falls into the class of plane-optical retroreflectors) is, for example, also known under the term "corner cube reflector". The realization of the reflection device that is based on this therefore has turned out to be particularly advantageous because the local coils (and therefore also their surfaces) normally do not lie planar relative to the plane of the recumbent board but rather are for the most part aligned at different angles to this reference plane per region. This is completely dependent on the non-planar surface of a test subject or, respectively, patient. The rectangular structure of the surfaces of the corner cube reflectors has therefore proven to be extremely advantageous because the angle of incidence given the reflection of the electromagnetic waves is practically identical to the angle of emergence. This relation retains its validity even up to an angle tolerance of ±45° in relation to the radiation direction of the incident electromagnetic waves.

Triple prisms also can be used. These are glass bodies that are flat on the front and on the back side possess three non-mirrored planar surfaces standing at an angle of 90° to one another. In contrast to a triple mirror, such a prism reflects with even less loss, and in fact even if the front side is not mirrored. The cause of this is the loss-free total reflection at the angled rear surfaces. Triple prisms in principle permit a greater deviation of their axis of symmetry from that of the radiation direction since the front surface of the glass body produces a refraction towards the vertical.

In the literature, angle reflectors are also known as radar reflectors that are produced from lead and reflect microwave rays.

Lüneburg lenses are the class of rotationally symmetrical retroreflectors. These are spheres made of a transparent material, mirrored on their back sides, with inhomogeneous index of refraction. They are also used as radar reflectors. Glass spheres whose material exhibits no homogeneous index of refraction and that throw a portion of the incident light back at the observer also fall into this class. In the event that a homogeneous index of refraction is present for the glass body, the shape must deviate from the spherical shape in order to realize a retroreflector.

Especially if a retroreflector is to be attached to the surface of the local coil, it is advantageous if a reflector foil is used. This is mechanically flexible and therefore can be easily adapted to the different curvatures of the local coil (which is ultimately defined by the body shape of the respective patient). Such reflector foils possess retroreflective pigments (for example transparent plastic balls) on their surface.

Items known as cat's-eye structures which can likewise be used also fall in the class of rotationally symmetrical retroreflectors. These are barrel-shaped glass bodies with a reflective coating on the back side.

In practically all embodiments of the invention, the detector system possesses a receiver device that is fashioned to receive the electromagnetic waves. This receiver device can be formed, for example, by photodetectors or other components (for example phototransistors, pyrometers or bolometers) that address or react to the electromagnetic waves. The receiver device is preferably located just next to the transmitter device. Narrowband filters can also be used in order to detect only waves of that frequency which should actually be evaluated.

According to a preferred exemplary embodiment of the invention, the receiver device has an image detection device (for example a camera) that is coupled with an image processing device. This realization in principle enables the detector system to be realized without a special reflection device. In this realization, the electromagnetic waves (for example visible light) can have been emitted from any arbitrary point in space and be reflected from the illustrated subject to be detected. In principle, any arbitrary light that is generated or present at any arbitrary point of the space in which the magnetic resonance tomography device is installed can be used. The signal source device therefore also does not need to be a component of the detector system of the magnetic resonance tomography device. Rather, it is possible to use the room lighting already present in the room or even natural light. The image detected with the aid of the image detection device is then output to the coupled image processing device and further processed there.

It has proven to be particularly advantageous in this context for the local coil to have a surface marking that can be visually detected and analyzed by the image detection device and the image processing device, i.e. with image evaluation methods. This surface marking can be formed, for example, as marking points or marking stripes that, in the present case, do not even need to be fashioned to be especially reflective but preferably can also be executed so as to diffusely scatter or also reflect.

In order to be able to process the signals received from the receiver device, the detector system has an evaluation device that is coupled with the receiver device and that is fashioned to evaluate the receiver signals with regard to the position of the local coil. The receiver signals thereby represent the electromagnetic waves received with the aid of the receiver device. In the case of the image detection and processing device—which can have on the receiver side a camera that can process visible or infrared light, for example—the evaluation device, downstream from the camera, has a device for image processing, a device for pattern recognition and—based on the pattern recognition—a device for coil type detection. This arrangement allows the coil position or the coil orientation to be precisely determined in addition to the detection of the coil type. The basis of this evaluation principle is thus an image of the patient with the local coils placed on him, generated with the use of a camera.

In the use of photodetectors as receivers for the electromagnetic waves, according to a further exemplary embodiment the evaluation device is fashioned to utilize at least one of the following parameters of the electromagnetic waves: delay, amplitude, phase, frequency, frequency shift. A combination of these parameters can also be used. However, other additional variables or properties can also be used in the evaluation, for example a displacement of the patient table relative to the transmission or reception device or reference markers. The evaluation device can be realized via separate electronic components provided for this comprising hardware or software. However, it has proven to be particularly advantageous when the electronic components (for example a modulator or a radio-frequency receiver that are provided for magnetic resonance measurement) that are already present in the magnetic resonance tomography device are used. This enables a cost-effective realization, in particular when a radio-frequency oscillator present in the magnetic resonance tomography device is advantageously used with which a laser diode is activated, for example, so that correspondingly modulated electromagnetic waves are radiated from the laser diode. These are reflected from the reflection device and then detected by a photodetector and transduced into a reception signal that is processed by a receiver of the magnetic resonance tomography device. This realization allows the detector system to detect the position of the local coil to integrate into the magnetic resonance tomography device with optimally little additional expenditure on hardware or, respectively, software and to reuse already present electronic components.

The previously explained elements of the detector system can be realized in different configurations in the magnetic resonance tomography device.

For example, in a first configuration a signal source device can be attached to the tomograph or, respectively, integrated into it and a receiver device can be provided on or in the local coil. The receiver signals generated by the receiver device can then be transmitted via a cable to the evaluation device, which can be attached to or integrated in the scanner.

According to a further configuration, the signal source device can be attached to or installed in the local coil and a receiver device can be attached to or integrated in the scanner. This second configuration is essentially complementary to the first configuration. In the present case, a connection between the evaluation device and the signal source device can be established to activate the signal source device so that said signal source device can be activated by the evaluation device. The reception signals generated by the receiver device are relayed directly to the evaluation device within the magnetic resonance tomography device.

In an additional configuration, a signal source device and a receiver device—thus both together—are provided at or integrated in the scanner, and a reflection device is installed on or in the local coil. This configuration is advantageous insofar as that no additional signal lines are necessary between the evaluation device (which preferably is also arranged within the magnetic resonance tomography device) and the local coil. The modifications to the local coil are in the present case limited to the attachment of a reflection device on the surface of the local coil.

In a further configuration, however, the signal source device and the receiver device can be provided at or integrated in the local coil, and the reflection device can be located on or in the scanner. The advantage of this configuration is that the reflection device attached to the tomograph always has a well-defined position and orientation in the magnetic resonance tomography device.

DESCRIPTION OF THE PREFERRED EMBODIMENTS

Figure 1:
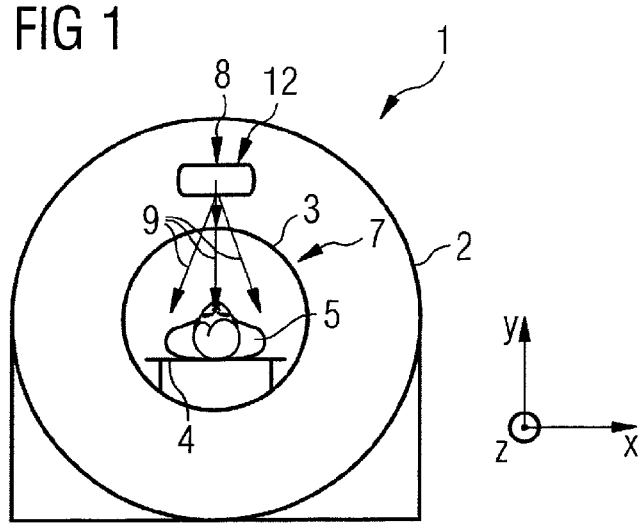
FIG. 1 schematically illustrates a magnetic resonance tomography device according to a first exemplary embodiment of the invention.

A magnetic resonance tomography device 1 (abbreviated in the following as an MRT device 1) according to a first exemplary embodiment of the invention is shown in FIG. 1, wherein only those components which are absolutely necessary to describe the invention are shown in detail. For the purpose of orientation, the coordinate system is also depicted with the x-direction, y-direction and z-direction.

The MRT device 1 possesses a scanner or, respectively, scanner 2 which houses the stationary magnet system and the RF transmission system of the MRT device 1. The scanner 2 possesses a measurement space 3 that is also known as a "bore" in the tech jargon. A bed 4 on which a patient 5 is positioned can be inserted into this measurement space 3 in order to acquire raw data in the known manner within the MRT device 1, wherein electromagnetic waves are generated in the form of a magnetic resonance signal. Volume image data are then later reconstructed in the typical manner from these raw data.

Figure 2:
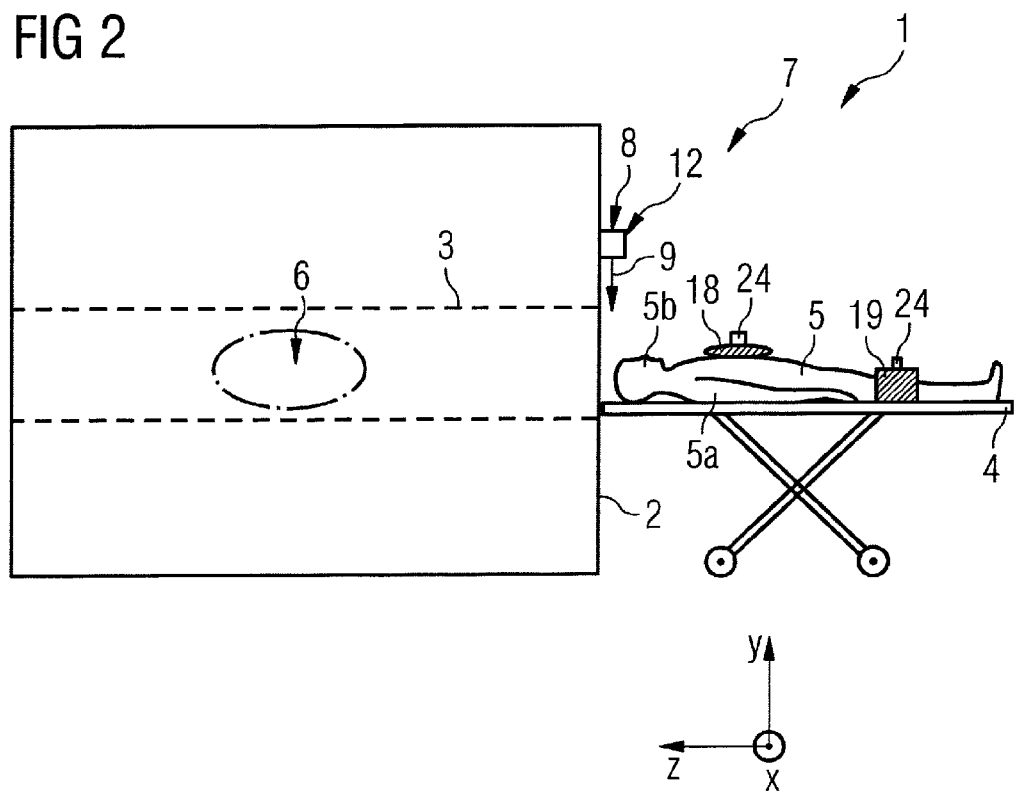
FIG. 2 shows the magnetic resonance tomography device according to FIG. 1 in a different perspective.

As shown in FIG. 2, a first local coil 18 and a second local coil 19 are placed on the body regions of the patient 5 that are to be examined. The arms $5a$ and head $5b$ of the patient 5 are additionally identified in order to clarify his orientation in the coordinate system of the MRT device 1. In order to acquire sufficiently good raw data (and thus qualitatively good image data), the patient 5 or that body region of the patient 5 from which exposures should be directly produced must come to lie optimally within a homogeneous volume 6 of the magnet system. The position of the homogeneity volume within the measurement space 3 is schematically depicted in FIG. 2.

The chest region of the patient 5 is covered by the first local coil 18, namely a cardiac coil, and a knee is covered by the second local coil 19, namely a knee coil.

In order to determine the position of the placed local coils 18 and 19, a detector system 7 is provided. This detector system 7 is fashioned to detect a position of the respective local coil 18 or 19 such that the detection is based on electromagnetic waves that are affected by the position of the local coil 18 or 19 and can be differentiated from or are different from the magnetic resonance signal that is emitted by the body 5 of the patient in a raw data acquisition.

The detector system 7 possesses a signal source device 8 that is fashioned to emit the electromagnetic waves 7. The signal source 8 in the present case is attached above the measurement space 3 at the scanner 2. However, at this point it is noted that the signal source device 8 can be located at any other point with a view of the bed 4 or, respectively, of the local coil 18 or, respectively, 19 to be detected. The signal source device 8 is in the present case realized with the aid of a laser diode 10 (see FIG. 3 and the following) with whose help the electromagnetic waves 9 can, for example, be emitted as visible light in the direction of the measurement space 3, as this is schematically shown in FIGS. 1 and 2 as well as 3 through 5.

Figure 3:
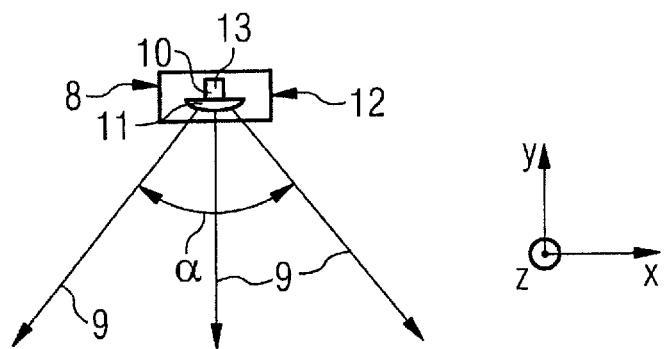
FIG. 3 shows a first exemplary embodiment of a signal source device and a receiver device of the magnetic resonance tomography device according to FIG. 1.
Figure 4:
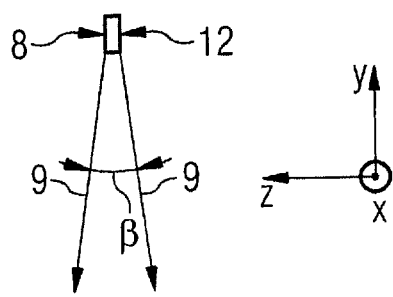
FIG. 4 shows the signal source device and receiver device according to FIG. 3 in a different perspective.

The signal source device 8 is explained again in detail in the following using FIGS. 3 and 4. As shown in FIG. 3, the signal source device 8 possesses the laser diode 10 and a lens 11 in the further beam path, placed in front of the laser diode 10. A beam that exhibits a first aperture angle $\alpha$ in a first direction (namely the x-direction) and—as is shown in FIG. 4—a second aperture angle $\beta$ in a second direction (namely the z-direction) can be generated with the aid of the lens 11. A wide illumination in relation to the x-direction and a relatively narrow-band illumination in relation to the z-direction (thus that direction in which the patient 5 with the bed 4 is inserted into the measurement space 3) can thus be achieved with the aid of the signal source device 8. As an example (but not limited to this), at this point it is specified that the first aperture angle $\alpha$ can assume a value in a range from 30° to 150° and the second aperture angle $\beta$ can assume a value in a range from 0.05° to 20°, such that the value of the second aperture angle $\beta$ is significantly smaller than the value of the first aperture angle $\alpha$. Accounting for the distance between the bed 4 and the signal source device 8, in the selection of a suitable value for the aperture angles $\alpha$ and $\beta$ it is to be considered as follows that the value of the aperture angle $\beta$ decides how widely or how much of the bed 4 or, respectively, of the patient 5 is illuminated along the x-direction, and the value of the aperture angle $\alpha$ decides how widely or how much of the bed 4 or of the patient 5 is illuminated along the z-direction.

Figure 6:
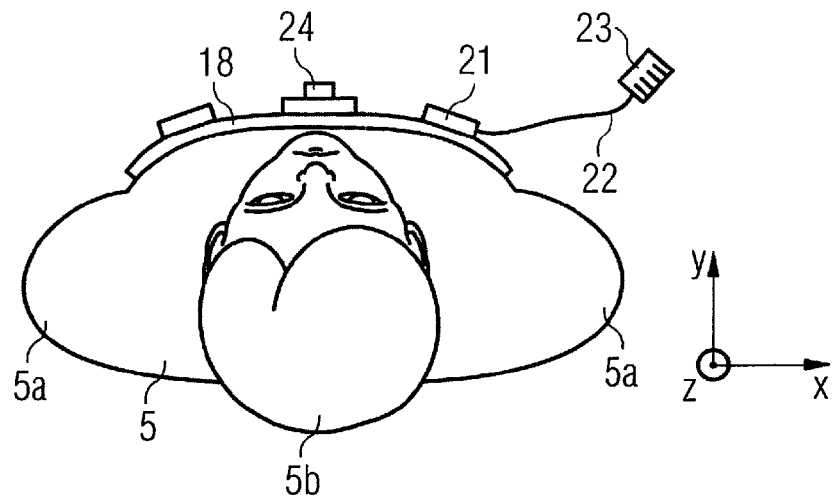
FIG. 6 schematically illustrates a reflection device mounted on a local coil.

In order to be able to use the electromagnetic waves 9 radiated by the signal source device 9 to detect the position of the local coils 18 and 19, the detector system 7 has a reflection examination volume 24 that—as shown in FIG. 6—is mounted on the outside of the local coil 18 and is fashioned to reflect the electromagnetic waves 9.

Located on the chest of the patient 5 (see FIG. 6) is the first local coil 18 that possesses elevations which indicate an electronic housing 21 that accommodates electronics of the local coil 18. Furthermore, a cable 22 that ends in a plug 23 with which the local coil 18 can be electrically connected with the MRT device 1 is a component of the local coil 18.

Figure 7:
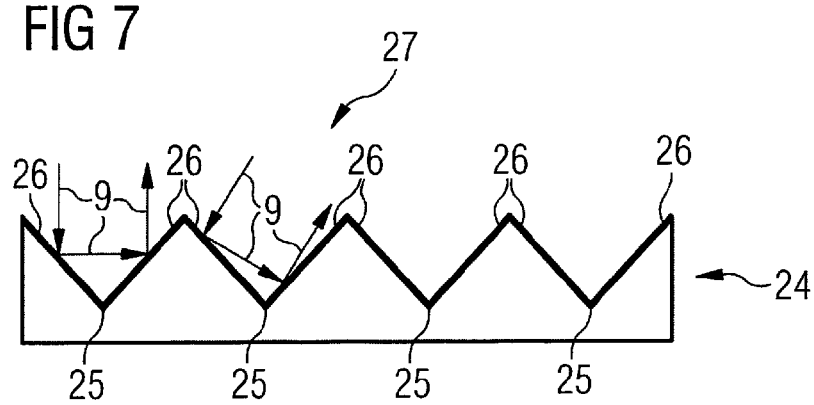
FIG. 7 is an enlarged section of the reflection device according to FIG. 6.

The reflection device 24 is schematically visualized in detail in FIG. 7. This is hereby a cross section through a portion of the reflection device 24. The reflection device 24 exhibits a surface structure. The surface structure is formed by three respective reflector surfaces 26 meeting in one corner 25 of a cube, which reflector surfaces 26 are realized by portions of inner surfaces of the cube. The inner surfaces are oriented open to the outside in relation to the reflection device 24 and act as mirrors for the electromagnetic waves 9. The reflector surfaces 6 are respectively arranged at an angle of 90° relative to one another. This surface structure is what is known as a retroreflector that is characterized in that the angle of incidence of the electromagnetic waves 9 is essentially equal to the angle of emittance of the reflected electromagnetic waves 9, which is illustrated by the beam path in the two left elements of the surface structure (incident waves 9—relayed from a left reflector surface 26 to a right reflector surface 26—emitted from this opposite to the direction of incidence).

Figure 22:
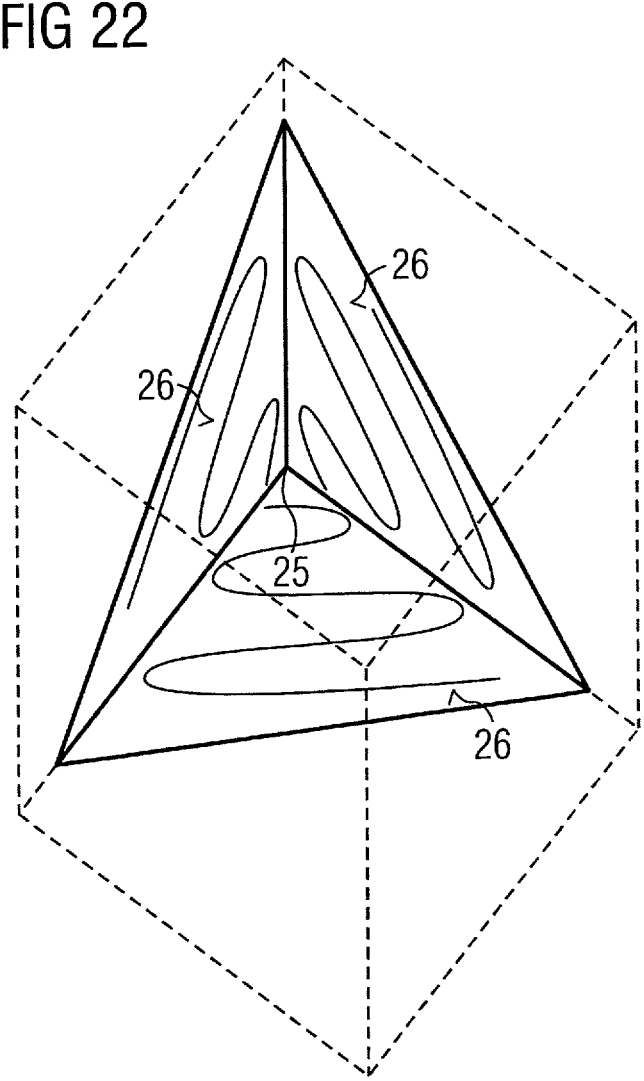
FIG. 22 is a schematic representation of an exemplary embodiment of a retroreflector.

A single element of the reflection device 24 is schematically shown in FIG. 22. From the cube visualized with its contour lines, the inner surfaces projecting into the depth of the plane of the drawing (or, respectively, more precisely stated, portions of these inner surfaces) form the three reflector surfaces 26 that are drawn hatched in the present case. The corner 25 of the cube that is common to the three reflector surfaces 26 forms the vertex of the cube that lies furthest to the rear in the depth of the plane of the drawing. With the exception of the hatched reflector surfaces 26, the surfaces or surface portions of the lateral faces of the cube are bounded at least on their sides by solid lines. A number of such elements arranged in a line forms the reflective region 27. The reflection can ensue either via a mirrored surface or via a complete reflection at a transition between media with different indices of refraction.

In order to detect the electromagnetic waves 9 reflected with the aid of the reflection device 24 and make an evaluation accessible, the detector 7 has a receiver device 12 that is fashioned to receive the electromagnetic waves 9. As is schematically shown in FIGS. 1 and 2, the receiver device 12 is essentially located at the same point or near that point at which the signal source device 8 is located. Typically the two devices 8 and 12 are housed or, respectively, integrated within a module (as this is shown in FIG. 3) so that it is then a combination of transmission device 8 and receiver device 12, whereupon in the following reference is made to it via the designation "combined transmission/reception device 8, 12". The receiver device 12 shown schematically in FIG. 3 has a photodiode 13 that is arranged positionally near to the laser diode 10 and adjacent to the lens 11.

If the patient 5 with the local coil 18 (on whose surface the reflection device 24 is located) positioned on him is now slid with the bed 4 (as this is shown in FIG. 2) below the combined transmission/reception device 8, 12 in the measurement space 3, the electromagnetic waves 9 emitted by the signal source device 8 are reflected back by the reflector device 24 in the direction of the signal source device 8 where they are received by the receiver device 12. Since the reflection device 24 possesses a limited extent in the z-direction (as this is illustrated in an exemplary embodiment according to FIG. 12A), the receiver device 12 generates a reception signal RS whose signal curve is visualized depending on the position of the first local coil 18 in the z-direction in FIG. 12B. The signal curve of the reception signal RS shows a maximum as soon as a reflective region 27 (whose cross section is shown in FIG. 7) is moved through the beam with the aperture angle $\beta$. The maximum of the reception signal RS occurs at the point Z0. This maximum indicates that the reflective region 27 is entirely located within the beam with the aperture angle $\beta$, thus precisely under the combined transmission/reception device 8, 12. A position correspondence in the z-direction thus exists at the position Z0 between the reflective region 27 and the combined transmission/reception device 8, 12. Since, first, the position of the bed 4 in the MRT device 1 is unambiguously known, and second the speed with which the bed 4 is introduced into the measurement space 3 is likewise known, when the first local coil 18 is localized within the homogeneity region 6 can be determined or predicted in an unambiguous manner with the assistance of the reception signal RS. The same analogously applies for the second local coil 19. Due to the use of the electromagnetic waves 9 (generated with the use of the signal source device 8) that is triggered by the magnetic resonance experiment, the position of the first local coil 18 can already be determined unambiguously outside of the measurement space 3.

Figure 5:
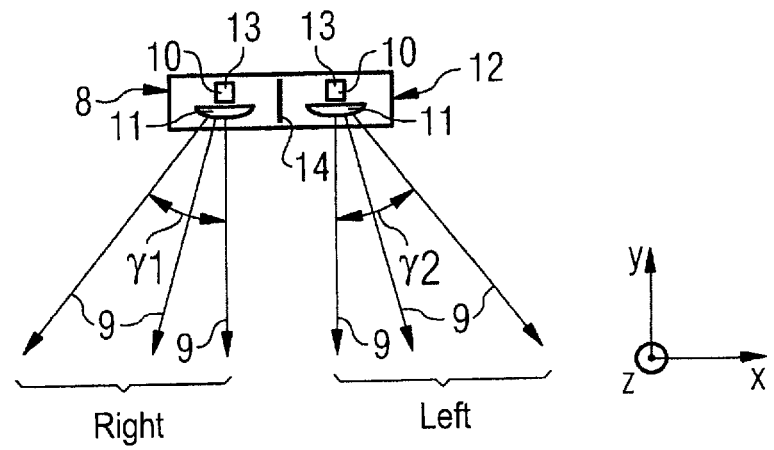
FIG. 5 shows a second embodiment of the signal source device and the receiver device of the magnetic resonance tomography device according to FIG. 1.

The unambiguous position of the second local coil 19 can now also be determined analogously. This ensues in the z-direction as explained in the preceding. However, for such a knee coil it is also important that it is established at which knee it is positioned (thus the left or right knee). This is achieved according to a further aspect of the invention as this is illustrated in FIG. 5, such that the signal source device 8 is fashioned to generate a first beam that covers a first direction region with a third aperture angle $\gamma_1$ and a second beam that covers a second direction region of the same direction with a fourth aperture angle $\gamma_2$. The orientation of the combined transmission/reception device 8, 12 is likewise illustrated in FIG. 5, wherein it arises that the third aperture angle $\gamma_1$ covers the right half of the bed width of the bed 4 in the x-direction and the fourth aperture angle $\gamma_2$ covers the left half of the bed width in the x-direction. The two aperture angles $\gamma_1$ and $y_2$ are selected so that their values are of approximately equal size on the one hand and, on the other hand, respectively cover approximately half of the first aperture angle $\alpha$. Since nothing changes at the second aperture angle $\beta$, the required relatively precise resolution in the z-direction is provide as before. However, a differentiation between left and right bed halves (and thus between the right and left knee of the patient 5) is additionally achieved. The realization of the combined transmission/reception device 8, 12 is based on employing two combined transmission/reception devices 8, 12 depicted in FIG. 3 next to each other. This can ensue with separate housings or by integration into a housing or a module—as shown in FIG. 5. However, in order to generate the two beams optimally without a mutual overlapping, on the one hand the alignment of the respective laser diode 10 or, respectively, the design of the respective lens 11 can be adapted and on the other hand a diaphragm 14 can be provided between the two parts. In order to achieve an additional resolution in one of the directions, more than two such combined transmission/reception devices 8, 12 can also be provided. These can (but do not need to) be located at the same point or in a module.

Figure 12A:
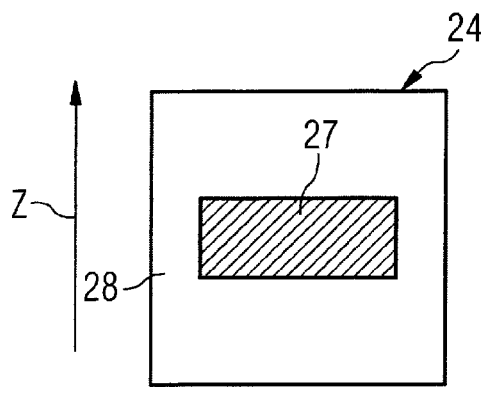
FIG. 12A shows a fifth embodiment of the encoding structure.
Figure 12B:
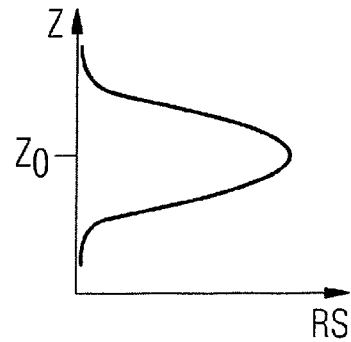
FIG. 12B shows a signal curve of a reception signal generated based on the fifth embodiment of the encoding structure according to FIG. 12A.

As already mentioned and as shown in FIG. 12A, the reflection device 24 can be realized via a band-shaped formation of a reflective region 27 that is surrounded by a non-reflective or less reflective region 28. This less reflective or non-reflective region 28 can also already be an integral component of the surface of the local coil 18 or 19. If, in addition the position of the coil, other information (for example orientation or type of coil) is important, as this is frequently the case if multiple such local coils 18 or, respectively, 19 are positioned on a patient, it can be advantageous when the reflection device 24 possesses an encoding structure that allows an encoding of the reflected electromagnetic waves with regard to one of the aforementioned parameters. A few such encoding structures are illustrated in FIGS. 9 through 10 and 12A, 13A and 14A, which are discussed in the following.

Figure 8:
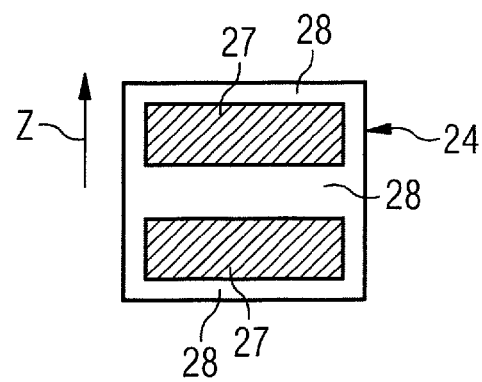
FIG. 8 shows a first embodiment of an encoding structure realized with the use of the reflection device according to FIG. 7.
Figure 9:
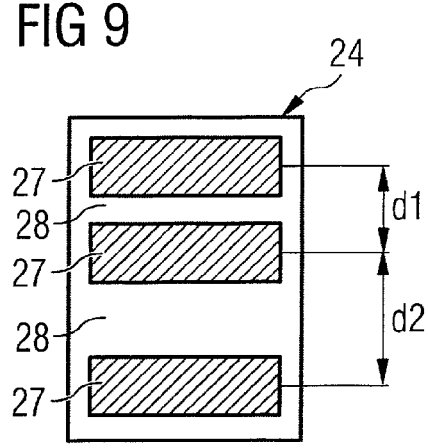
FIG. 9 shows a second embodiment of the encoding structure.
Figure 10:
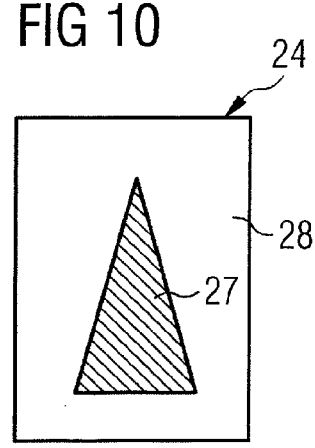
FIG. 10 shows a third embodiment of the encoding structure.
Figure 11:
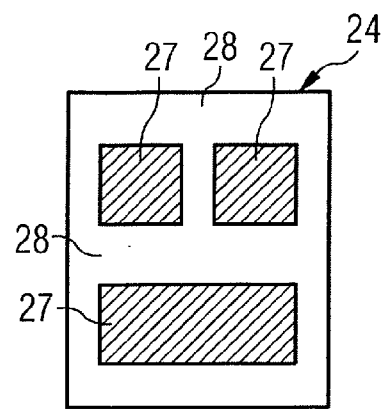
FIG. 11 shows a fourth embodiment of the encoding structure.
Figure 13A:
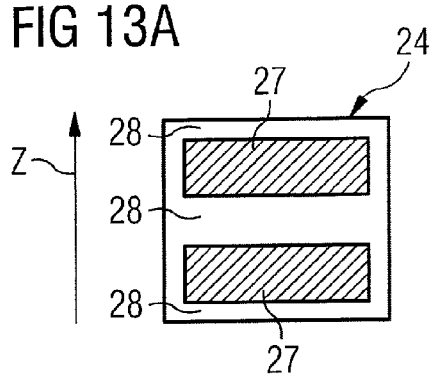
FIGS. 13A and 13B show signal curves of the reception signal generated according to the first embodiment of the encoding structure.
Figure 13B:
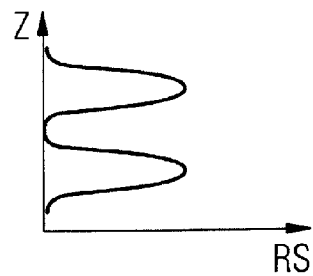
Figure 14A:
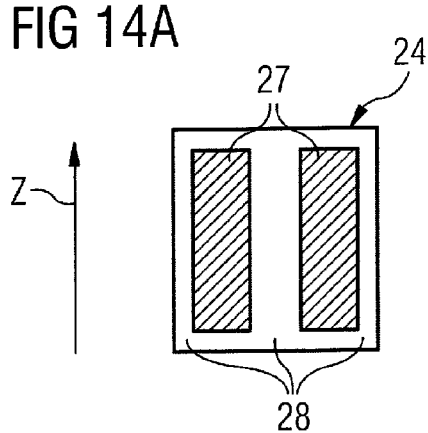
FIGS. 14A and 14B show signal curves of the reception signal generated according to the first embodiment of the encoding structure rotated by 90°.
Figure 14B:
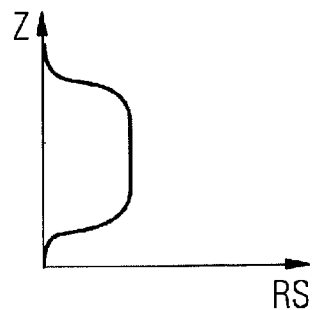

FIG. 8 shows two reflective regions 27 located at a distance from one another in the z-direction that are fashioned in the shape of bars. In contrast to this, the reflection device 24 according to FIG. 9 shows three reflective regions 27 that are, however, positioned at different intervals relative to one another (see first interval d1 and second interval d2). Shown in FIG. 10 is a reflective region 27 fashioned like an arrow that, for example, can lead to an increase or ebbing of the intensity of the reception signal RS if it is directed through the beam. In contrast to the reflective region 27 shown in FIG. 8 and arranged at the top with regard to the plane of the drawing, the reflective region 27 shown at the top in FIG. 11 is sub-divided into two sub-regions. On the basis of the signal diagram shown in FIG. 12B, the movement of the encoding structure shown in FIG. 8 in the z-direction (as this is shown in FIG. 13A) yields a signal curve of the reception signal RS according to FIG. 13B. In contrast to the signal curve shown in FIG. 12B, two maxima occurring in temporal succession are now formed. In FIG. 14A the bar-shaped reflective regions 27 shown in FIG. 8 are now aligned parallel to the z-direction. Therefore a signal curve for the reception signal RS results according to FIG. 14B. Which orientation the respective local coil 18 or 19 has in relation to the z-direction can thus be unambiguously determined via a simple comparison of the two signal curves according to FIG. 13B and FIG. 14B. An arbitrary encoding depth can be achieved in principle depending on the complexity of the reflective regions 27 and the non-reflective regions 28, such that not only the position or the orientation of the local coil 18, 19 or 20 but also its type can be unambiguously detected, and in fact without having to exchange electrical signals via a line between the local coil 18, 19 or 20 and the MRT device 1 (which electrical signals explicitly specify the type of the local coil 18, 19 or 20). The respective local coil 18, 19 or 20 thus does not need to have any complicated electronics in order to be able to communicate with the MRT device 1 with regard to the determination of its type.

Figure 18:
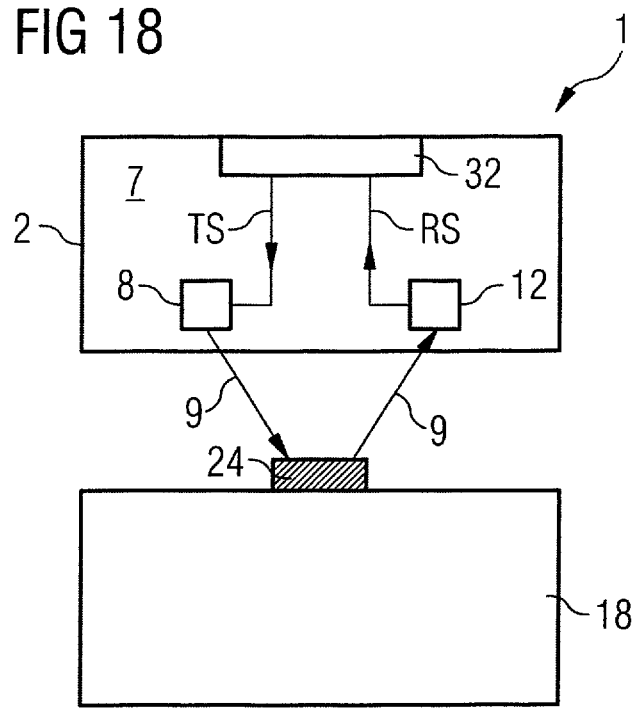
FIG. 18 shows a first exemplary embodiment of a configuration of the magnetic resonance tomography device according to the invention.
Figure 19:
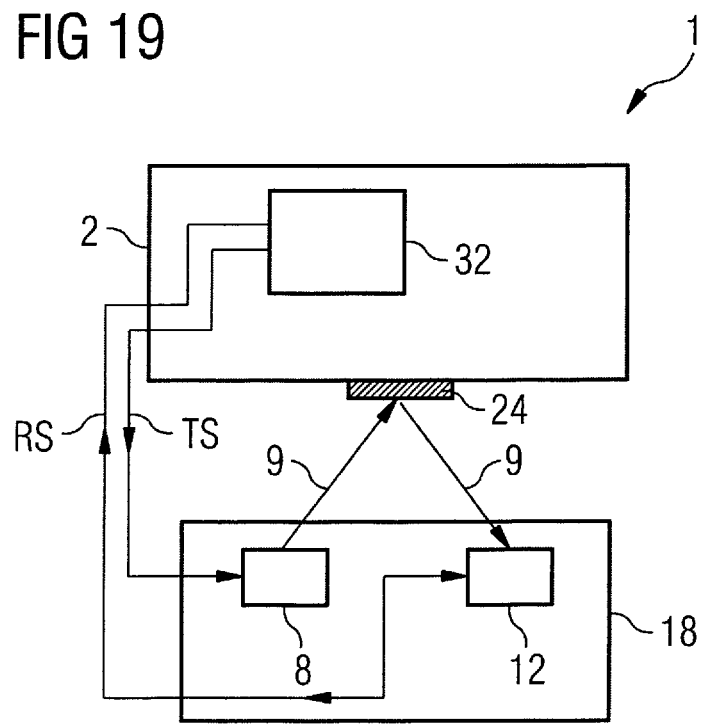
FIG. 19 shows a second exemplary embodiment of a configuration of the magnetic resonance tomography device according to the invention.

The previously explained principle of the emission of electromagnetic waves 9, the reflection and ultimately the reception of these electromagnetic waves 9 can be realized via at least two configurations that are depicted in FIGS. 18 and 19. That configuration that is shown in FIG. 1 and FIG. 2 is visualized in a strongly schematic manner in FIG. 18. The electromagnetic waves 9 are thereby emitted from the signal source device 8 attached to the scanner 2 and are reflected back to the scanner 2 with the aid of the reflection device 24 attached to the first local coil 18. In FIG. 18 it is additionally shown that the detector system 7 possesses an evaluation device 32 that is coupled with the receiver device 12 and that is fashioned to evaluate the reception signal RS with regard to the position of the local coil 18. However, it should be noted that other parameters—for example delay or phase or frequency or frequency shift or combinations of these—can also be used.

An additional configuration which utilizes the reflection principle is depicted in FIG. 19. In contrast to the configuration depicted in FIG. 18, the electromagnetic waves 9 are now emitted from the local coil 18 in which the signal source device 8 is installed and are reflected back to the first local coil 18 by the reflection device 24 that, in the present case, is attached to the scanner 2. In contrast to the configuration shown in FIG. 18, a wiring between the evaluation device 32 and the first local coil 18 (or the signal source device 8 installed in it) and the receiver device 12 is now necessary.

Figure 20:
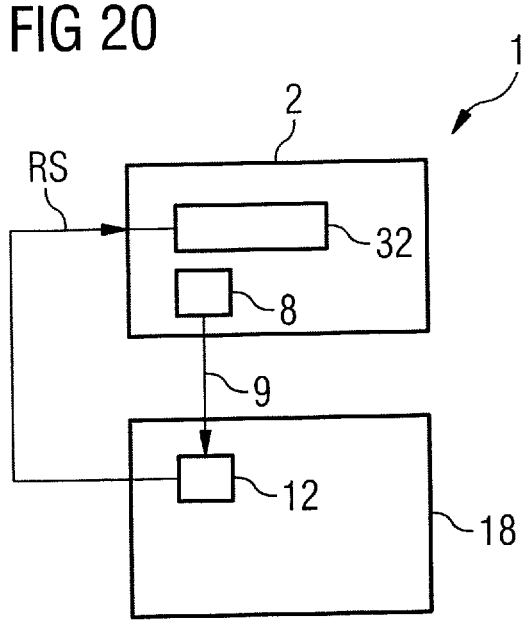
FIG. 20 shows a third exemplary embodiment of a configuration of the magnetic resonance tomography device according to the invention.
Figure 21:
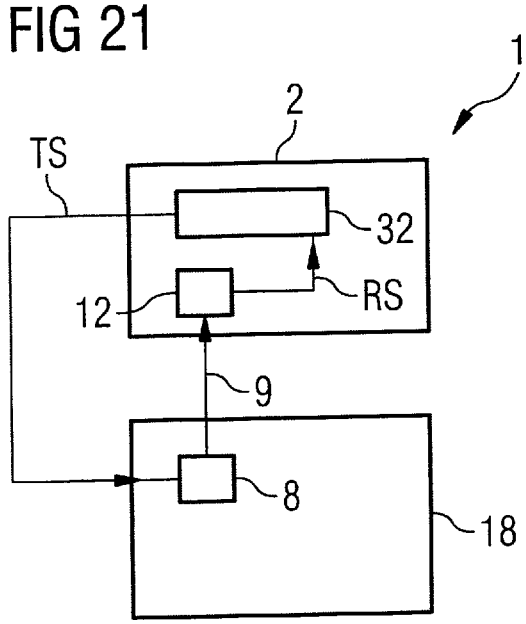
FIG. 21 shows a fourth exemplary embodiment of a configuration of the magnetic resonance tomography device according to the invention.

Following the basic idea of the invention, according to which the detection is based on electromagnetic waves 9 that are caused or affected by the position of a local coil 18, 19 or 20 and can be differentiated from the magnetic resonance signal, at this point two additional configurations are to be noted that are shown in FIGS. 20 and 21. According to the configuration depicted in FIG. 20, the signal source device 8 is located on the scanner 2 and the receiver device 12 is located in the first local coil 18. The receiver device 12 is connected via a cable with the evaluation device 32 in order to emit the reception signal RS to the receiver device 12. In contrast to this, the configuration depicted in FIG. 21 is designed such that the receiver device 12 is located at the scanner 2 and the signal source device 8 is located in the first local coil 18. In the present case, a cable connection likewise exists between the evaluation device 32 and the signal source device 8, with which the transmission signal TS is output to the signal source device 8.

Figure 15:
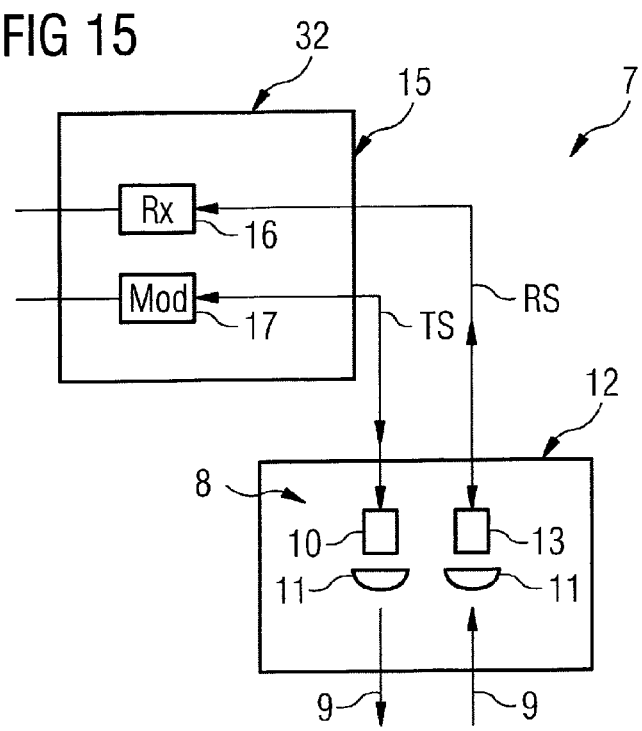
FIG. 15 illustrates an evaluation device formed by a signal processor of the magnetic resonance tomography device according to the invention.

According to a preferred exemplary embodiment of the invention, the evaluation device 32 is realized with the aid of signal processing means 15 of the MRT device 1, which is roughly schematically presented in FIG. 15. In this Figure only the output-side and input-side signal processing means 15 are shown, which on the one hand are a receiver 16 and on the other hand are a modulator 17 that are also used in magnetic resonance experiments or, respectively, the raw data acquisition. Additional elements of the signal processing means 15 are not shown in detail; however, they can also form components of the evaluation device 32. In the present case, the modulator 17 can be used to trigger the laser diode 10 in order to generate the electromagnetic waves 9. The receiver 16 is used to receive the reception signal RS generated by the photodetector in order to make it accessible for a further processing.

Figure 16:
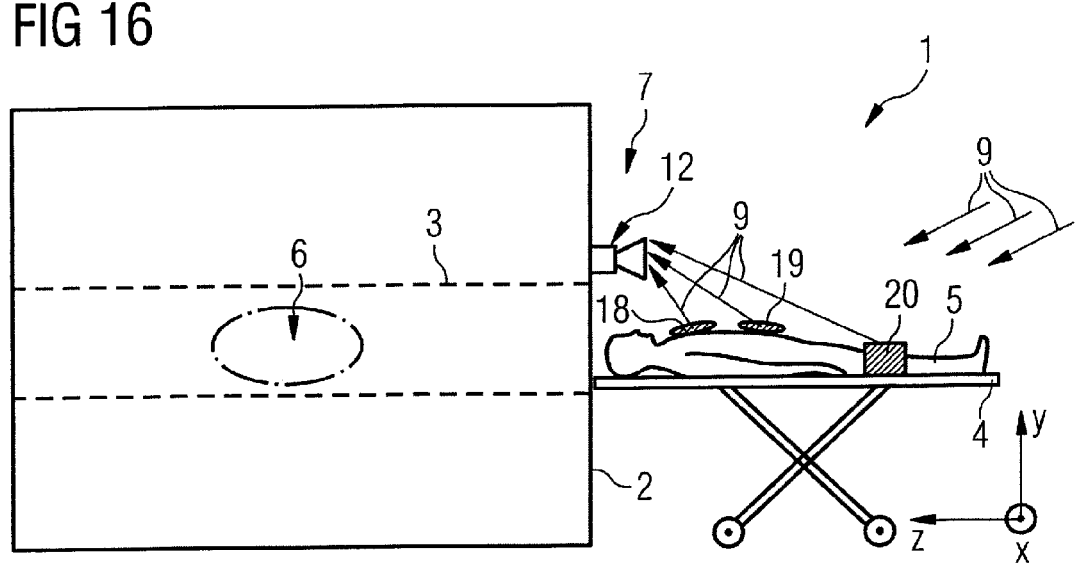
FIG. 16 analogous to FIG. 1, schematically illustrates a magnetic resonance tomography device according to a second exemplary embodiment of an invention.
Figure 17:
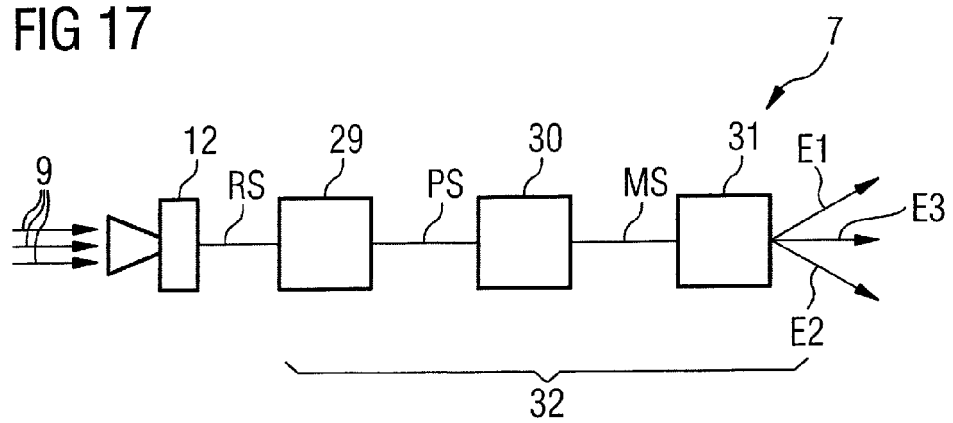
FIG. 17 schematically illustrates an evaluation device of the magnetic resonance tomography device according to FIG. 16.

A further exemplary embodiment of the invention, is schematically visualized in FIGS. 16 and 17. According to this exemplary embodiment, the receiver device 12 is realized (with the aid of an image detection device) in the form of a camera that is coupled with an image processing device 29. The camera enables a detection of images based on the electromagnetic waves (for example in the form of visible light) that are reflected from the body or from the local coils 18, 19 and 20 positioned on the patient 5. In the present case, a signal source device 8 and associated electronics have thus been completely omitted, contrary to which the receiver device 12 and the evaluation device 32 downstream of this are possibly of more complicated design. As a result of the receipt of the electromagnetic waves 9, the camera generates the reception signal RS and outputs thus to an image processing device 29. Based on the reception signal RS, the image processing device 29 generates an image data signal PS which represents the image or, respectively, the scene detected with the aid of the camera and outputs this to a pattern recognition device 30 in which a pattern recognition occurs in the image detected with the aid of the camera 12. The pattern recognition device 30 or its part outputs the detected pattern in the form of a pattern data signal MS to a result mapping device 31 that, based on the received patter data signal MS, is fashioned to output a first result data signal E1 which represents the coil position of the respective local coil 18 through 20, a second result data signal E2 which represents the coil orientation of the respective local coil 18 through 20 and a third result data set E3 which represents the respective coil type of the local coil 18 through 20. A requirement for this deep analysis of the image detected with the aid of the camera can be that the respective local coil 18, 19 or 20 possesses a surface structure or, respectively, surface marking that can be visually detected and processed with the aid of the devices 12, 29, 30 and 31, for example the reflection device 24 (which, however, is not necessarily the case in the present case because here the angle of incidence of the waves 9 will typically unequal to the angle of emittance).

According to the invention, a method according to the invention to detect the position of the local coil 18, 19 and 20 in an MRT device 1 can be implemented with the aid of the structural methods described in the preceding, which local coil 18, 19 or 20 is fashioned to receive a magnetic resonance signal, wherein the detection of the position of the respective local coil 18, 19 or 20 ensues based on the electromagnetic waves 9 that can be differentiated from the magnetic resonance signal, as this was described in detail.

It is noted that the different aperture angles $\alpha$, $\beta$, $\gamma_1$ and $\gamma_2$ can be realized by a suitable design of the lens 11 and/or by a suitable design of diaphragms and/or collimators within the module and/or in the region of the exit aperture of the respective beam, which however is not shown in detail in the figures.

Furthermore, it is noted that not only the position of the local coil 18, 19 or 20 in the z-direction or in the x-direction can be determined; rather, the position in the y-direction can also be detected via suitable positioning of the transmitter device 8 or the receiver device 12, for example on the periphery of the measurement space 3 or via a corresponding design of the reflection device 24. A common transmission signal TS or individual transmission signals TS and/or a common reception signal RS or individual reception signals RS can thereby be used in order to determine the position in the cross section of the measurement space 3 with the use of the evaluation unit 32, thus in the plane spanned by the x-direction and the y-direction.

It is additionally noted at this point that, although certain realizations have been explained using only one direction (for example the x-direction), these realizations can also extend to other directions. For example, a segmentation into multiple beams can also occur in the z-direction or in the y-direction.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance tomography apparatus comprising:
    a magnetic resonance data acquisition unit configured to acquire magnetic resonance data from an examination subject located in an opening in said magnetic resonance data acquisition unit that has a longitudinal axis along which the examination subject is moved through the opening, said longitudinal axis coinciding with the z-direction of a Cartesian coordinate system in which the x-direction is substantially horizontal and the z-direction is substantially vertical;
    said magnetic resonance data acquisition unit comprising a local coil configured to receive a magnetic resonance signal during acquisition of said magnetic resonance data;
    a detector system configured to detect a position of the local coil on the examination subject using electromagnetic waves that are differentiatable from said magnetic resonance signal, said detector system comprising a source that emits said electromagnetic waves in a radiation field, and a reflection device located in said radiation field, on which said electromagnetic waves are incident with a direction of incidence, and that reflects said electromagnetic waves in a reflection direction that substantially coincides with, but is opposite to, said direction of incidence;
    said signal source and said reflector being located at respective locations relative to each other that cause said reflected electromagnetic waves to be affected by the position of the local coil as said examination subject, with the local coil thereon, is moved into the data acquisition unit; and
    said signal source being configured to emit a beam of said electromagnetic waves having a first aperture angle in said x-direction and a second aperture angle in said z-direction, thereby causing said detector system to detect a peak of the reflected electromagnetic waves as coinciding with the position of the coil as the examination subject is moved into the magnetic resonance data acquisition unit.

2. A magnetic resonance tomography apparatus as claimed in claim 1 wherein said detector system is configured to process optically propagating electromagnetic waves.

3. A magnetic resonance tomography apparatus as claimed in claim 1 wherein said signal source emits said electromagnetic waves in said radiation field in order to interact with said local coil.

4. A magnetic resonance tomography apparatus as claimed in claim 1 wherein said signal source is configured to emit said electromagnetic waves in a first beam encompassing a first region in a first direction and in a second beam encompassing a second region in a second direction.

5. A magnetic resonance tomography apparatus as claimed in claim 1 wherein said reflection device has an encoding structure that encodes at least one type of information selected from the group consisting of the position of the local coil, an orientation of the local coil, and a type of said local coil.

6. A magnetic resonance tomography apparatus as claimed in claim 1 wherein said detector system comprises a receiver configured to receive said electromagnetic waves after said electromagnetic waves interact with said local coil.

7. A magnetic resonance tomography apparatus as claimed in claim 6 wherein said receiver comprises an image detection device coupled to an image processing device.

8. A magnetic resonance tomography apparatus as claimed in claim 7 wherein said local coil comprises a surface marking that is visually detectable, and wherein said image detection device is configured to detect said surface marking and said image processing device is configured to process said surface marking.

9. A magnetic resonance tomography apparatus as claimed in claim 8 wherein said image processing device comprises an evaluation module connected to said receiver device and configured to evaluate signals received by said receiver device in order to identify the position of the local coil.

10. A magnetic resonance tomography apparatus as claimed in claim 9 wherein said evaluation module is configured to utilize at least one characteristic of said electromagnetic waves, selected from the group consisting of delay, amplitude, phase, frequency and frequency shift, in order to identify said position of said local coil.

11. A magnetic resonance tomography apparatus as claimed in claim 1 wherein said signal source is located on or in said data acquisition unit and said receiver device is located on or in said local coil.

12. A magnetic resonance tomography apparatus as claimed in claim 1 wherein said signal source is located on or in said local coil, and said receiver is located on or in said data acquisition unit.

13. A method to detect a position of a local coil in a magnetic resonance tomography apparatus, comprising the steps of:
    placing a local coil on an examination subject, said local coil being configured to receive a magnetic resonance signal in a magnetic resonance data acquisition unit;
    moving the examination subject into an opening in the magnetic resonance data acquisition unit with the local coil on the examination subject, said opening having a longitudinal axis along which the examination subject is moved through the opening, said longitudinal axis coinciding with the z-direction of a Cartesian coordinate system in which the x-direction is substantially horizontal and the z-direction is substantially vertical;
    detecting a position of said local coil using electromagnetic waves that are affected by a position of the local coil and that are differentiatable from said magnetic resonance signal by emitting said electromagnetic waves from a radiation source in a radiation field in which a reflector having a retroreflective surface is located on the local coil, and reflecting said electromagnetic waves from said retroreflective surface in a reflection direction that is substantially coincident with, and opposite to, a direction of incidence of said electromagnetic waves on said retroreflective surface; and
    placing said signal source and said reflector at respective locations relative to each other that cause said reflected electromagnetic waves to be affected by the position of the local coil as said examination subject, with the local coil thereon, is moved into the data acquisition unit; and from said signal source, emitting a beam of said electromagnetic waves having a first aperture angle in said x-direction and a second aperture angle in said z-direction, thereby causing said detector system to detect a peak of the reflected electromagnetic waves as coinciding with the position of the coil as the examination subject is moved into the magnetic resonance data acquisition unit.

* * * * *